United States Patent [19]  
Green

[11] 3,980,680  
[45] Sept. 14, 1976

[54] PROCESS FOR THE PREPARATION OF 21-DESOXY-17-ACYLOXY-4-PREGNENES AND OF 21-IODO-21-DESOXY-17-ACYL OXY-4-PREGNENE INTERMEDIATES USEFUL THEREIN

[75] Inventor: Michael J. Green, East Brunswick, N.J.

[73] Assignee: Schering Corporation, Kenilworth, N.J.

[22] Filed: Aug. 14, 1975

[21] Appl. No.: 604,671

[52] U.S. Cl. .......................................... 260/397.45
[51] Int. Cl.$^2$............................................ C07J 5/00
[58] Field of Search .............................. 260/397.45

[56] References Cited
UNITED STATES PATENTS

| | | | |
|---|---|---|---|
| 3,796,701 | 3/1974 | Cimaruste et al. | 260/239.55 D |
| 3,798,217 | 3/1974 | Ackrell et al. | 260/239.55 D |

*Primary Examiner*—Elbert L. Roberts  
*Attorney, Agent, or Firm*—Mary S. King

[57] ABSTRACT

21-Desoxy-17α-acyloxy-20-keto-4-pregnenes having physiological properties are prepared by the reaction of a 17α,21-dihydroxy-20-keto-4-pregnene 17α,21-orthoester or a 21-iodo-21-desoxy-17α-acyloxy-20-keto-4-pregnene with an iodide reagent selected from the group consisting of triphenylsilyl iodide, tri-lower alkylsilyl iodide and triphenylmethyl iodide. When said 17α,21-dihydroxy-20-keto-4-pregnene 17α,21-orthoester is reacted with less than two molar equivalents of a tri-lower alkylsilyl iodide reagent there is also formed a 21-iodo-21-desoxy-17-α-acyloxy-20-keto-4-pregnene, a useful intermediate, which, upon reaction with additional iodide reagent, is converted to the corresponding 21-desoxy-17α-acyloxy-20-keto-4-pregnene.

10 Claims, No Drawings

PROCESS FOR THE PREPARATION OF 21-DESOXY-17-ACYLOXY-4-PREGNENES AND OF 21-IODO-21-DESOXY-17-ACYL OXY-4-PREGNENE INTERMEDIATES USEFUL THEREIN

FIELD OF INVENTION

This invention relates to a novel process for the manufacture of 21-desoxy-17α-acyloxy-20-ketopregnenes.

More specifically, this invention relates to the process for preparing 21-desoxy-17α-hydrocarboncarbonyloxy-20-keto-4-pregnenes which are known, physiologically active steroids from 17α,21-dihydroxy-20-keto-4-pregnene 17α,21-orthoesters. By this process, under certain conditions, are also prepared 21-iodo-21-desoxy-17α-hydrocarboncarbonyloxy-20-keto-4-pregnenes which are known, useful intermediates.

PRIOR ART

Known in the art are 21-desoxy-17α-acyloxy-20-keto-4-pregnenes and the 1-dehydro-, 6-dehydro-, and 1,6-bis-dehydro analogs thereof which possess progestational, glucocorticoid and anti-inflammatory activities.

Prior art methods for preparing the 21-desoxy-17α-acyloxy-20-keto-4-pregnenes from 17α,21-dihydroxy-20-keto-4-pregnenes involve multistep sequences of reactions. One method comprises converting a 17α,21-dihydroxy-20-keto-4-pregnene to the corresponding 17α,21-orthoester followed by acid hydrolysis thereof to a 17α-acyloxy-20-keto-21-hydroxy-4-pregnene, thence conversion of the 21-hydroxy group to a 21-sulfonate ester followed by reaction of the 21-sulfonate ester with sodium iodide in acetic acid whereby is formed the corresponding 21-iodo derivative which is reduced in situ to give a 21-desoxy-17α-acyloxy-20-keto-4-pregnene.

Another method comprises the conversion of an 11β,17α,21-trihydroxy-4-pregnene-20-one to the corresponding 21-lower alkanoate, followed by esterification of the 11β-hydroxy to yield an 11β-nitrate 21-lower alkanoate derivative, thence hydrolysis of the 21-lower alkanoate followed by esterification of the 21-hydroxyl group with a sulfonic acid halide to yield an 11β-nitrate 21-sulfonate derivative, a key intermediate which may be transformed to an 11β-hydroxy-21-desoxy-17α-acyloxy-4-pregnene by one of the following three routes:

1. Treatment with sodium iodide in acetic acid followed by acylation of the resulting 21-desoxy-11β,17α-dihydroxy-4-pregnene-20-one 11β-nitrate and thence removal of the 11β-nitrate ester in the thereby formed 21-desoxy-11β,17α-dihydroxy-4-pregnene-20-one 11β-nitrate 17α-acylate by reaction with zinc dust and acetic acid, 2. Acylation at C-17 followed by treatment of the resulting 11β,17α,21-trihydroxy-4-pregnene-20-one 11β-nitrate 17α-acylate 21-sulfonate with zinc in acetic acid to give the corresponding 11β-hydroxylated compound which, upon treatment with sodium iodide in acetic acid, yields a 21-desoxy-11β-hydroxy-17α-acyloxy-4-pregnene-20-one, 3. Treatment of the 11β,17α,21-trihydroxy-4-pregnene-20-one 11β-nitrate 17α-acylate 21-sulfonate intermediate of the foregoing method with sodium iodide in acetic acid followed by treatment of the resulting 21-desoxy-11β,17α-dihydroxy-4-pregnene-20-one 11β-nitrate 17α-acylate with zinc in acetic acid to obtain a 21-desoxy-11β-hydroxy-17α-acyloxy-4-pregnene-20-one.

Not only do the prior art methods involve a multitude of reaction steps but also the acylation of the 17-hydroxyl group requires forcing conditions which may cause acylation of the 11β-hydroxyl group or aromatization of the A-ring unless the 11β-hydroxy and/or 3-keto functions are protected.

By the process of this invention, good yields of pure 21-desoxy-17α-acyloxy-20-keto-4-pregnenes are quickly and easily obtained in one step from the 17α,21-orthoester by reaction with a triphenylsilyl iodide or a tri-lower alkylsilyl iodide without the necessity of protecting other functional groups (e.g. the 3-ketone or 11β-hydroxyl) present in the molecule and thence removal of the protecting groups when the process is completed.

In my copending applications, Ser. Nos. 604,672 and 604,673, filed Aug. 14, 1975 are described and claimed processes for preparing a 21-chloro (or bromo)-17α-acyloxy-20-ketopregnene from a 17α,21-orthoester utilizing triphenylmethyl chloride (or bromide), triphenylsilyl chloride (or bromide) or a tri-lower alkylsilyl chloride (or bromide) as reagent. By the instant invention I have discovered that when the corresponding iodide reagents are employed, the 21-iodo intermediate, upon formation, is immediately reduced in situ to the 21-desoxy-17α-acyloxy-20-keto-4-pregnene so that when at least two molar equivalents of iodide reagent is employed per mole of 17α,21-orthoester, there is isolated only 21-desoxy-17α-acyloxy-20-keto-4-pregnene in good yields. Alternatively, when a 17α,21-dihydroxy-20-keto-4-pregnene is reacted with less than two molar equivalents of a tri-lower alkylsilyl iodide reagent, a mixture of 21-desoxy and 21-iodo-21-desoxy-17α-acyloxy-20-keto-4-pregnenes are formed. Conversion of the 21-iodo-21-desoxy derivative to the corresponding 21-desoxy-17α-acyloxy-20-ketopregnene is easily effected by reaction thereof with additional iodide reagent.

GENERAL DESCRIPTION OF THE INVENTION

The process of this invention, whereby a 17α,21-dihydroxy-20-ketopregnene 17α,21-orthoester is converted to a 21-desoxy-17α-acyloxy-20-ketopregnene is defined as the process for the preparation of a 21-desoxy-17α-acyloxy-20-ketopregnene which comprises the reaction of a pregnene derivative selected from the group consisting of a 17α,21-dihydroxy-20-ketopregnene-17α,21-orthoester and a 21-iodo-21-desoxy-17α-acyloxy-20-ketopregnene with an iodide reagent selected from the group consisting of triphenylsilyl iodide, tri-lower alkylsilyl iodide and triphenylmethyl iodide, in an organic solvent.

Of the 21-desoxy-17α-acyloxy-20-ketopregnenes prepared by the process of this invention, those specifically contemplated include 4-pregnenes of the following formula I and the 1-dehydro-, 6-dehydro-, and 1,6-bis-dehydro analogs thereof:

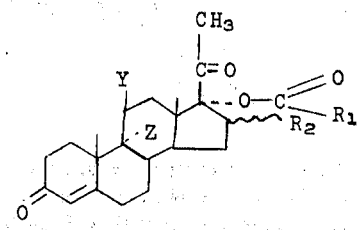

I wherein Y is hydrogen, oxo, hydroxy, lower alkanoyloxy, chlorine or fluorine;

Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;

$R_1$ is alkyl of 1 to 8 carbon atoms, or phenyl; and $R_2$ is hydrogen, α-methyl, β-methyl, α-acyloxy of the formula

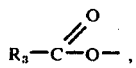

wherein $R_3$ is a lower alkyl having 1 to 8 carbon atoms.

The foregoing are known compounds possessing, in general, progestational, glucocorticoid and anti-inflammatory activities and, as such, can be used in the same manner as other known progestational and anti-inflammatory agents.

Thus, included among the compounds prepared by my process are 9α,11β-dihalogeno-17α-alkanoyloxyprogesterones of formula I, their 16-methyl and 16α-lower alkanoyloxy derivatives and the 1-dehydro-, 6-dehydro-, and 1,6-bis-dehydro analogs thereof which are valuable mainly as progestational agents. The 9α,11β-dihalogeno-17-alkanoyloxyprogesterone derivatives specifically contemplated include 9α-bromo-11β-chloro-17α-alkanoyloxyprogesterones, 9α-bromo-11β-fluoro-17α-alkanoyloxyprogesterones, 9α-chloro-11β-fluoro-17α-alkanoyloxyprogesterones and, in particular, 9α,11β-dichloro-17α-alkanoyloxyprogesterones such as 9α,11β-dichloro-1,4-pregnadiene-11β,17α-diol-20-one 17-propionate (i.e. 9α,11β-dichloro-17α-propionyloxy-1-dehydroprogesterone), 9α,11β-dichloro-16α-methyl-1,4-pregnadiene-17α-ol-20-one 17-propionate, 9α,11β-dichloro-16α-methyl-1,4-pregnadiene-17α-ol-20-one 17-benzoate and 9α,11β-dichloro-16α-methyl-1,4-pregnadiene-17α-ol-20-one 17-valerate which are potent progestational agents.

Other valuable progestational agents of formula I which are prepared by my process include 17α-alkanoyloxy progesterones, their 16-methyl and 16-lower alkanoyloxy derivatives, and the 1-dehydro-, 6-dehydro-, and 1,6-bis-dehydro analog thereof.

The 11-oxygenated compounds of formula I, particularly the 11β-hydroxyl derivatives, and the 1-dehydro-, 6-dehydro-, and 1,6-bis-dehydro analogs thereof, are particularly useful as topical anti-inflammatory agents, a preferred group of compounds being the 1-dehydro analogs of the 11β-hydroxy compounds of formula I, particularly those defined by following formula II:

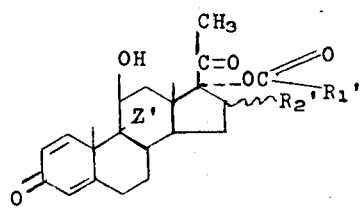

II wherein Z' is hydrogen or fluorine;
$R_1'$ is alkyl of 1 to 4 carbon atoms; and
$R_2'$ is hydrogen, α-methyl or β-methyl.

Particularly valuable topical anti-inflammatory compounds of formula II which are prepared by my process include 1,4-pregnadiene-11β,17α-diol-3,20-dione 17-propionate, 9α-fluoro-16α-methyl-1,4-pregnadiene-11β,17α-diol-3,20-dione 17-propionate, and 9α-fluoro-16β-methyl-1,4-pregnadiene-11β,17α-diol-3,20-dione 17-propionate.

In addition to the foregoing, by my process, when less than two molar equivalents of a tri-lower alkylsilyl iodide per mole of 17α,21-orthoester starting steroid is utilized, there is formed in admixture with the 21-desoxy compounds, the 21-iodo derivatives of formula I which are known compounds, valuable as intermediates in preparing the corresponding 21-chloro, 21-bromo, 21-azido, 21-phosphate, or 21-desoxy progesterones via procedures known in the art.

In the process of this invention, whereby a 17α,21-dihydroxy-20-ketopregnene 17α,21-orthoester is reacted with an iodide reagent to produce a 21-desoxy-17α-alkanoyloxy-20-ketopregnene, the iodide reagents used are known compounds made via known procedures. Typical reagents include triphenylsilyl iodide, trimethylsilyl iodide, triethylsilyl iodide, tri-(n-propyl)-silyl iodide, tri-(n-butyl)silyl iodide and triphenylmethyl iodide. Of the foregoing, least desirable is triphenylmethyl iodide since it is difficult to prepare and easily decomposes. Of the preferred reagents for this process, when an excess of a tri-lower alkylsilyl iodide reagent is reacted with an 11β,17α,21-trihydroxy-20-ketopregnene 17α,21-orthoester, there may also be formed the 11-trialkylsilyl ether of the 21-desoxy-11β-hydroxy-17α-alkanoyloxy-20-ketopregnene thereby produced. Conversion of the 11-trialkylsilyl ether to the corresponding 11β-hydroxy derivative is effected via acid hydrolysis. Additionally, when less than two molar equivalents of a tri-lower alkylsilyl halide per mole of 17α,21-orthoester starting compound is used in my process, the resulting product is a mixture of 21-desoxy-17α-alkanoyloxy-20-keto-4-pregnene and the co-produced, corresponding 21-iodo derivative. Separation of the product mixture can be effected by chromatographic techniques and the isolated 21-iodo compound is easily convertible to the corresponding 21-desoxy derivative by reaction with an additional quantity of iodide reagent according to the process of this invention.

In contrast, triphenylsilyl iodide reagent may be used in excess with an 11-hydroxylated starting compound without the formation of undesired 11-triphenylsilyl ether side products. Additionally, when triphenylsilyl halide is used as reagent, the 17α,21-orthoester is converted in high yields to the 21-desoxy-17α-alkanoyloxy-20-keto-4-pregnene product free of any co-produced 21-iodo derivative even when only equimolar quantities of steroidal 17α,21-orthoester and iodide reagent are utilized. Thus, triphenylsilyl iodide is a reagent of choice when carrying out my process with an 11-hydroxylated 17α,21-orthoester.

When carrying out my process, to obtain maximum yields of 21-desoxy-17α-alkanoyloxy-20-keto-4-pregnene, the starting 17α,21-orthoester must be reacted with at least two moles of iodide reagent. By adding the 17α,21-orthoester to a solution of the iodide reagent, there is maximized the probability of complete reaction, since the added orthoester is thereby always in the presence of excess iodide reagent until one mole of orthoester has been added per two moles of iodide reagent.

My process is preferably carried out in an organic solvent in which both the steroid starting compound and the reagents are soluble and which will not react with the reagent so that competing side reactions are minimized. Suitable organic solvents for this process include 1,2-dimethoxyethane (glyme); bis(2-methoxyethyl)ether (diglyme); cyclic ethers such as dioxane and tetrahydrofuran; and preferably halogenated hydrocarbons such as carbon tetrachloride, chloroform, ethylene dichloride and, in particular, methylene chloride.

My process is usually carried out at room temperature and is completed in less than 30 minutes as determined by thin layer chromatography. When trimethylsilyl iodide is utilized as reagent, the reaction occurs almost instantaneously, so that when the starting orthoester has an 11β-hydroxyl group, it is necessary to immediately isolate the 21-desoxy-17α-alkanoyloxy-20-ketopregnene thereby formed in order to minimize the formation of the 11-trimethylsilyl ether side product. The 21-desoxy-17α-alkanoyloxy-20-ketopregnene products are conveniently isolated by washing the reaction mixture with dilute aqueous sodium thiosulfate then with water, drying the washed solution, and evaporating in vacuo to a residue comprising the 21-desoxy product which may be purified utilizing standard techniques, preferably thin layer chromatography.

My process is advantageously run under anhydrous conditions and may be carried out under an inert atmosphere, e.g. under argon or nitrogen; however, this is not necessary.

The requisite starting compounds of my process are 17α,21-orthoesters of the 17α,21-dihydroxy analogs of the compounds defined by formula I. The orthoesters are obtained from the corresponding 17α,21-dihydroxy-20-ketopregnene by known reaction with a trialkyl orthoester in a polar organic solvent, e.g. dimethylformamide or dimethylsulfoxide, in the presence of an acid catalyst, e.g. p-toluenesulfonic acid. The reaction may be carried out under an inert atmosphere, e.g. nitrogen or argon, but this is not necessary. The reaction is usually carried out at room temperature for a period of time ranging from 2 to 24 hours; however, when preparing a 17α,21-alkylorthobenzoate, the reaction is preferably carried out in benzene/dioxane at reflux temperature.

Specifically, the starting compounds of my process include 17α,21-dihydroxy-20-ketopregnene 17α,21-orthoesters having the following formula III:

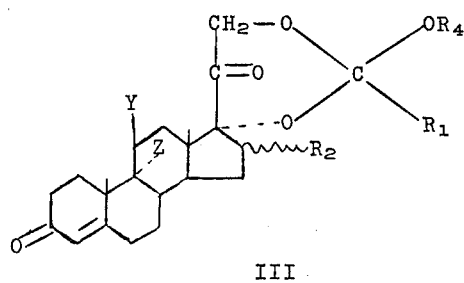

III wherein Y is hydrogen, oxo, hydroxy, lower alkanoyloxy, chlorine or fluorine;

Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;

$R_1$ is alkyl of 1 to 8 carbon atoms, or phenyl;

$R_2$ is hydrogen, α-methyl, β-methyl, α-acyloxy of the formula

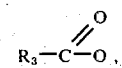

wherein $R_3$ is lower alkyl having 1 to 8 carbon atoms;

$R_4$ is alkyl having 1 to 4 carbon atoms; and the 1-dehydro-, 6-dehydro- and 1,6-bis-dehydro analogs thereof.

Compounds of formula II are made by reaction of the corresponding 17α,21-dihydroxy steroid with a trialkyl orthoester of the formula

wherein $R_1$ is alkyl of 1 to 8 carbon atoms or phenyl; and $R_4$ is an alkyl of 1 to 4 carbon atoms.

In a preferred mode of carrying out my process of preparing a 21-desoxy-17α-alkanoyloxy-20-ketopregnene, to one mole of a steroidal 17α,21-orthoester of formula III in a halogenated solvent (usually methylene chloride) there is added at least two moles (and usually about 3 moles of triphenylsilyl iodide or about 5 moles of trimethylsilyl iodide per mole of steroid) of a reagent selected from the group consisting of triphenylsilyl iodide, tri-lower alkylsilyl iodide and triphenylmethyl iodide, preferred reagents being triphenylsilyl iodide or trimethylsilyl iodide. The reaction is stirred at room temperature (optionally under an inert atmosphere) for a few minutes until the reaction is completed as determined by thin layer chromatography (usually less than 30 minutes). The resulting 21-desoxy-17α-acyloxy-20-keto-4-pregnene is then isolated as described herein in excellent yields and purified utilizing conventional techniques, such as via chromatographic techniques or by crystallization.

The following examples illustrate specific embodiments of the invention, but are not to be considered as limiting the scope of the invention, obvious equivalents of which, apparent to one skilled in the art, being considered as included within the scope of this invention.

PREPARATION OF INTERMEDIATES

PREPARATION 1

9α,11β-Dichloro-16α-Methyl-1,4-Pregnadiene-17α,21-Diol-3,20-Dione 17,21-methylorthobenzoate and the 1,2-Dihydro Analog thereof A. To a solution of 2 gms. of 9α,11β-dichloro-16α-methyl-1,4-pregnadiene-17α,21-diol-3,20-dione in 112 ml. of dioxane and 168 ml. of benzene add 2 ml. of trimethylorthobenzoate and 200 mg. of pyridinium p-toluenesulfonate and heat at reflux temperature for 24 hours. Add an additional 2 ml. portion of trimethylorthobenzoate and 200 mg. of pyridinium-p-toluenesulfonate and heat at reflux temperature for 3 more days. Distill off about two-thirds of the solvent, add about 6 drops of pyridine and then distill the remaining solvent in vacuo at room temperature. Triturate the resulting residue with petroleum ether and decant the petroleum ether wash to obtain a residue comprising 9α,11β-dichloro-16α-methyl-1,4-pregnadiene-17α,21-diol-3,20-dione 17,21-methylorthobenzoate, which is used without further purification in the process of this application.

B. In a manner similar to that described in above Preparation 1A, treat 9α,11β-dichloro-16α-methyl-4- pregnene-17α,21-diol-3,20-dione in dioxane and benzene with trimethylorthobenzoate and pyridinium p-toluenesulfonate; evaporate the solvents, then wash the resultant product with petroleum ether in a manner similar to that described to obtain 9α,11β-dichloro-16α-methyl-4-pregnene-17,21-diol-3,20-dione 17,21-methylorthobenzoate.

PREPARATION 2

1,4-Pregnadiene-11β,17α,21-Triol-3,20-Dione 17,21-n-Butylorthopropionate and the 1,2-Dihydro Analog Thereof A. To a solution of 2 gms. of 1,4-pregnadiene-11β,17α,21-triol-3,20-dione in 10 ml. of dimethylsulfoxide add 150 mg. of p-toluenesulfonic acid and 3.6 ml. of tri-n-butylorthopropionate. Stir the reaction mixture at room temperature for 3.5 hours, then pour onto 600 ml. of ice water to which has been added 300 ml. of saturated sodium bicarbonate solution. Separate the resultant precipitate by filtration and wash the precipitate with copious amounts of water. Dissolve the precipitate in ethyl acetate. Dry the ethyl acetate solution over anhydrous magnesium sulfate and evaporate in vacuo to a residue comprising 1,4-pregnadiene-11β,17α,21-triol-3,20-dione 17,21-n-butylorthopropionate.

B. In similar manner, treat 4-pregnene-11β,17α,21-triol-3,20-dione in dimethylsulfoxide with p-toluenesulfonic acid and tri-n-butylorthopropionate to obtain 4-pregnene-11β,17α,21-triol-3,20-dione 17,21-n-butylorthopropionate.

PREPARATION 3

9α,11β-Dichloro-16α-Methyl-1,4-Pregnadiene-17α,21-Diol-3,20-Dione 17,21-n-butylorthopropionate and the 1,2-Dihydro Analog Thereof A. To a solution of 2 gm. of 9α,11β-dichloro-16α-methyl-1,4-pregnadiene-17α,21-diol-3,20-dione in 12 ml. of dimethylsulfoxide add 150 mg. of p-toluenesulfonic acid and 3.6 ml. of tri-n-butylorthopropionate. Stir the reaction mixture at room temperature for 4 hours, then pour onto 600 ml. of ice water, to which has been added 300 ml. of saturated sodium bicarbonate solution. Separate the resultant precipitate by filtration and wash the precipitate with copious amounts of water. Dissolve the precipitate in ethyl acetate, dry the ethyl acetate over anhydrous magnesium sulfate and evaporate in vacuo to a residue comprising 9α,11β-dichloro-16α-methyl-1,4-pregnadiene-17α,21-diol-3,20-dione 17,21-n-butylorthopropionate.

B. In similar manner, treat 9α,11β-dichloro-16α-methyl-4-pregnene-17α,21-diol-3,20-dione in dimethylsulfoxide with p-toluenesulfonic acid and tri-n-butylorthopropionate to obtain 9α,11β-dichloro-4-pregnene-17α,21-diol-3,20-dione 17,21-n-butylorthopropionate.

PREPARATION 4

9α,11β-Dichloro-16α-Methyl-1,4-Pregnadiene-17α,21-Diol-3,20-Dione 17,21-n-butylorthovalerate and the 1,2-Dihydro Analog Thereof A. To a solution of 2 gm. of 9α,11β-dichloro-16α-methyl-1,4-pregnadiene-17α,21-diol-3,20-dione in 12 ml. of dimethylsulfoxide add 150 mg. of p-toluenesulfonic acid and 4 ml. of tri-n-butylorthovalerate. Stir at room temperature for 4 hours, then add 600 ml. of ice water, to which has been added 300 ml. of saturated sodium bicarbonate. Isolate the resultant product in a manner similar to that described in Preparation 3A to obtain 9α,11β-dichloro-16α-methyl-1,4-pregnadiene-17α,21-diol-3,20-dione 17,21-n-butylorthovalerate.

B. Treat a solution of 9α,11β-dichloro-16α-methyl-4-pregnene-17α,21-diol-3,20-dione in dimethylsulfoxide with p-toluenesulfonic acid and tri-n-butylorthovalerate in a manner similar to that described hereinabove to obtain 9α,11β-dichloro-16α-methyl-4-pregnene-17α,21-diol-3,20-dione-3,20-dione 17,21-n-butylorthovalerate.

PREPARATION 5

9α-Fluoro-16β-Methyl-1,4-Pregnadiene-11β,17α,21-Triol-3,20-Dione 17, 21-n-Butylorthopropionate and the 1,2-Dihydro Analog Thereof A. In a manner similar to that described in Preparation 2A, treat 3 gm. of 9α-fluoro-16β-methyl-1,4-pregnadiene-11β,17α,21-triol-3,20-dione in 9 ml. of dimethylsulfoxide with 225 mg. of p-toluenesulfonic acid and 5.4 ml. of tri-n-butylorthopropionate at room temperature for 4 hours. Isolate and purify the resultant product in a manner similar to that described to obtain 9α-fluoro-16β-methyl-1,4-pregnadiene-11β,17α,21-triol-3,20-dione 17,21-n-butylorthopropionate.

B. In a manner similar to that described hereinabove, treat 9α-fluoro-16β-methyl-4-pregnene-11β,17α,21-triol-3,20-dione in dimethylsulfoxide with p-toluenesulfonic acid and tri-n-butylorthopropionate to obtain 9α-fluoro-16β-methyl-4-pregnene-11β,17α,21-triol-3,20-dione 17,21-n-butylorthopropionate.

PREPARATION 6

16α-Methyl-1,4-Pregnadiene-11β,17α,21-Triol-3,20-Dione 17,21-n-butylorthopropionate and the 1,2-Dihydro Analog Thereof A. To a solution of 0.75 gm. of 16α-methyl-1,4-pregnadiene-11β,17α,21-triol-3,20-dione in 3.75 ml. of dimethylsulfoxide add 56.5 mg. of p-toluenesulfonic monohydrate and 2.25 ml. of tri-n-butylorthopropionate and stir the reaction mixture at room temperature for 3 hours. Pour into a mixture of 400 ml. of ice water and 100 ml. of saturated sodium bicarbonate solution. Decant the aqueous layer and triturate the gummy residue with hexane. Separate the resultant precipitate by filtration and dry at room temperature in vacuo to obtain 16α-methyl-1,4-pregnadiene-11β,17α,21-triol-3,20-dione 17,21-n-butylorthopropionate (yield 0.87 gm.).

B. In a manner similar to that described hereinabove, treat 16α-methyl-4-pregnene-11β,17α,21-triol-3,20-dione in dimethylsulfoxide with p-toluenesulfonic monohydrate in tri-n-butylorthopropionate and isolate the resultant product in the described manner to obtain 16α-methyl-4-pregnene-11β,17α,21-triol-3,20-dione 17,21-n-butylorthopropionate.

PREPARATION 7

9α-Fluoro-16α-Methyl-1,4-Pregnadiene-11β,17α,21-Triol-3,20-Dione 17,21-Methylorthobenzoate and the 1,2-Dihydro Analog Thereof A. To 1 gm. of 9α-fluoro-16α-methyl-1,4-pregnadiene-11β,17α,21-triol-3,20-dione in 64 ml. of dioxane and 84 ml. of benzene add 1 ml. of trimethylorthobenzoate and 100 mg. of pyridinium p-toluenesulfonate.

Heat the reaction mixture at reflux temperature for 3 days, then distill two-thirds of the solvent at atmospheric pressure, add 5 drops of pyridine, then distill the remaining solvent in vacuo at room temperature. Triturate the resultant residue with petroleum ether and filter the resultant solid comprising 9α-fluoro-16α-methyl-1,4-pregnadiene-11β,17α,21-triol-3,20-dione 17,21-methylorthobenzoate.

B. Treat 9α-fluoro-16α-methyl-4-pregnene-11β,17α,21-triol-3,20-dione in dioxane and benzene with trimethylorthobenzoate and pyridinium p-toluenesulfonate in the manner described hereinabove to obtain 9α-fluoro-16α-methyl-4-pregnene-11β,17α,21-triol-3,20-dione 17,21-methylorthoenzoate.

PREPARATION 8

9α-Fluoro-16α-Methyl-1,4-Pregnadiene-11β,17α, 21-Triol-3,20-Dione 17,21-n-Butylorthopropionate and the 1,2-Dihydro Analog Thereof A. In a manner similar to that described in Preparation 6A, treat 9α-fluoro-16α-methyl-1,4-pregnadiene-11β,17α,21-triol-3,20-dione in dimethylsulfoxide with p-toluenesulfonic monohydrate and tri-n-butylorthopropionate. Isolate and purify the 9α-fluoro-16α-methyl-1,4-pregnadiene-11β,17α,21-triol-3,20-dione 17,21-n-butylorthopropionate.

B. In a manner similar to that described hereinabove, treat 9α-fluoro-16α-methyl-4-pregnene-11β,17α,21-triol-3,20-dione in dimethylsulfoxide with p-toluenesulfonic monohydrate and tri-n-butylorthopropionate to obtain 9α-fluoro-16α-methyl-4-pregnene-11β,17α,21-triol-3,20-dione 17,21-n-butylorthopropionate.

PREPARATION 9

1,4,6-Pregnatriene-11β,17α, 21-Triol-3,20-Dione 17,21-n-Butylorthopropionate and the 1,2-Dihydro Analog Thereoof A. To a solution of 60 mg. of 1,4,6-pregnatriene-11β,17α,21-triol-3,20-dione in 0.5 ml. of dimethylsulfoxide add 5 mg. of p-toluenesulfonic acid and 0.3 ml. of tri-n-butylorthopropionate. Stir at room temperature for 3 hours, pour into saturated sodium bicarbonate solution and extract with ethyl acetate. Dry the combined ethyl acetate extracts over magnesium sulfate, then evaporate in vacuo to a residue comprising 1,4,6-pregnatriene-11β,17α,21-triol-3,20-dione 17,21-n-butylorthopropionate.

B. In a manner similar to that described hereinabove, treat 4,6-pregnadiene-11β,17α,21-triol-3,20-dione in dimethylsulfoxide with p-toluenesulfonic acid and tri-n-butylorthopropionate to obtain 4,6-pregnadiene-11β,17α,21-triol-3,20-dione 17,21-n-butylorthopropionate.

PREPARATION 10

9α-Fluoro-16β-Methyl-17α,21-Diol-3,11,20-Trione 17,21-methylortho-n-butyrate and the 1,2-Dihydro Analog Thereof A. In a manner similar to that described in Preparation 4A, treat 9α-fluoro-16β-methyl-1,4-pregnadiene-11β,17α-diol-3,11,20-trione in dimethylsulfoxide with p-toluenesulfonic acid and trimethylortho-n-butyrate. Isolate and purify the resultant product in a manner similar to that described to obtain 9α-fluoro-16β-methyl-11β,17α-diol-3,11,20-trione 17,21-methylorthobutyrate.

B. In a manner similar to that described hereinabove, treat 9α-fluoro-16β-methyl-4-pregnene-17α,21-diol-3,11,20-trione in dimethylsulfoxide with p-toluenesulfonic acid and trimethylortho-n-butyrate to obtain 9α-fluoro-16β-methyl-4-pregnene-17α,21-diol-3,11,20-trione 17,21-methylortho-n-butyrate.

PREPARATION 11

6α,9α-Difluoro-16β-Methyl-1,4-Pregnadiene-11β,17α,21-Triol-3,20-Dione 17,21-Ethylorthoacetate and the 1,2-Dihydro Analog Thereof A. In a manner similar to that described in Preparation 5A, treat 6α,9α-difluoro-16β-methyl-1,4-pregnadiene-11β,17α,21-triol-3,20-dione in dimethylsulfoxide with p-toluenesulfonic acid and triethylorthoacetate. Isolate and purify the resultant product in a manner similar to that described to obtain 6α,9α-difluoro-16β-methyl-1,4-pregnadiene-11β,17α,21-triol-3,20-dione 17,21-ethylorthoacetate.

B. In a manner similar to that described hereinabove, treat 6α,9α-difluoro-16β-methyl-4-pregnene-11β,17α,21-triol-3,20-dione in dimethylsulfoxide with p-toluenesulfonic acid and triethylorthoacetate to obtain 6α,9α-difluoro-16β-methyl-4-pregnene-11β,17α,21-triol-3,20-dione 17,21-ethylorthoacetate.

EXAMPLE 1

1,4-PREGNADIENE-11β,17α-DIOL-3,20-DIONE

A. Addition of Triphenylsilyl Iodide (3 equivalents) to the 17,21-Orthoester

1. To a solution of 1,4-pregnadiene-11β,17α,21-triol-3,20-dione 17,21-ethylorthopropionate (96 mg.) in methylene chloride (1 ml.) add triphenylsilyl iodide (255 mg., 3 equivalents). Stir at room temperature for 10 minutes, then wash the solution with 0.1 N aqueous sodium thiosulfate, then with water. Dry the methylene chloride solution over magnesium sulfate, evaporate in vacuo and purify the resultant solid by chromatographing on silica gel by thin layer technique developing with chloroform/ethyl acetate (2:1). Scrape off the band containing 1,4-pregnadiene-11β,17α-diol-3,20-dione 17-propionate as shown by ultraviolet light, elute with ethyl acetate and evaporate the ethyl acetate to a residue comprising 1,4-pregnadiene-11β,17α-diol-3,20-dione 17-propionate; yield 37 mg. (43% theory); m.p. 216°–219°C; $[\alpha]_D^{26}$ + 32.1° (chloroform).

2. In similar manner treat 1,4-pregnadiene-11β,17α,21-triol-3,20-dione 17,21-n-butylorthopropionate with triphenylsilyl iodide and isolate the resultant product in a manner similar to that described to obtain 1,4-pregnadiene-11β,17α-diol-3,20-dione 17-propionate.

B. Addition of Trimethylsilyl Iodide (5 equivalents) to the 17,21-Orthoester

1. To a solution of 1,4-pregnadiene-11β,17α,21-triol-3,20-dione 17,21-ethylorthopropionate (100 mg.) in methylene chloride (2.5 ml.) add trimethylsilyl iodide (225 mg. = 0.153 ml., 5 equivalents). After 30 seconds wash the solution with 0.1 N aqueous sodium thiosulfate, then with water, dry over magnesium sulfate, evaporate in vacuo and purify the resultant solid residue on silica gel via thin layer technique developing the plates with chloroform/ethyl acetate (2:1). Scrape off the band containing 1,4-pregnadiene-11β,17α-diol-3,20-dione 17-propionate as shown by ultraviolet light and elute with ethyl acetate. Evaporate the eluates, add ether to the resultant residue and filter to obtain 1,4-pregnadiene-11β,17α-diol-3,20-dione 17-propionate, yield 62 mg. (69% theory). Further purify by adding ether to the residue and filter the resultant crystalline precipitate, yield 40 mg. (45% theory); m.p. (and mixed m.p. with authentic sample) 222°–226°C; $[\alpha]_D^{26}$ + 40° (chloroform)

2. In similar manner treat 1,4-pregnadiene-11β,17α,21-triol-3,20-dione 17,21-n-butylorthopropionate with trimethylsilyl iodide to obtain 1,4-pregnadiene-11β,17α-diol-3,20-dione 17-propionate.

C. Addition of the 17,21-Orthoester to Trimethylsilyl Iodide (1 equivalent)

To a mixture of trimethylsilyl iodide (0.0306 ml., 1 equivalent) in methylene chloride (1 ml.). Add dropwise over a period of 1 minute a solution of 1,4-pregnadiene-11β,17α,21-triol-3,20-dione 17,21-ethylorthopropionate (100 mg.) in methylene chloride. Stir for 10 minutes, then wash the solution with 0.1 N aqueous sodium thiosulfate, then with water, dry over magnesium sulfate and evaporate in vacuo to a residue comprising 1,4-pregnadiene-11β,17α-diol-3,20-dione 17-propionate. Purify by chromatographing on silica gel via thin layer developing with chloroform/ethyl acetate (9:1). Scrape off the band containing the desired product as shown by ultraviolet light, elute with ethyl acetate and evaporate in vacuo to a residue of 1,4-pregnadiene-11β,17α-diol-3,20-dione 17-propionate, yield 10 mg. (12% theory).

D. Addition of 17,21-Orthoester to Trimethylsilyl Iodide (2 equivalents)

1. To a solution of trimethylsilyl iodide (0.3006 ml., 2 equivalents) in methylene chloride (7.5 ml.) under an atmosphere of nitrogen. Add dropwise over a period of 1 minute a solution of 1,4-pregnadiene-11β,17α,21-triol-3,20-dione 17,21-ethylorthopropionate (0.5 gm.) in methylene chloride (2 ml.). Stir an additional 10 minutes at room temperature, then wash with 0.1 N aqueous sodium thiosulfate, then water. Dry over magnesium sulfate and evaporate in vacuo. Chromatograph the resultant residue on a silica gel column (50 gm.) eluting with chloroform/ethyl acetate (20:1). Combine the like fractions as determined by thin layer chromatography. Evaporate the first set of like fractions to a residue comprising 1,4-pregnadiene-11β,17α-diol-3,20-dione 11-trimethylsilyl ether 17-propionate, yield 160 mg. (30% theory). Evaporate the combined like later fractions to a residue comprising 1,4-pregnadiene-11β,17α-diol-3,20-dione 17-propionate, yield 60 mg. (13% theory).

2. Dissolve the 160 mg. of 1,4-pregnadiene-11β,17α-diol-3,20-dione 11-trimethylsilyl ether 17-propionate obtained as described in Example 1D(1) in 15 ml. of methanol, add 2.25 ml. of 6 N hydrochloric acid. Allow the solution to stand at room temperature for 25 hours, then add water, filter off the resultant precipitate, wash the precipitate with water and dry to obtain 1,4-pregnadiene-11β,17α-diol-3,20-dione 17-propionate.

E. Addition of Trimethylsilyl Iodide (1 equivalent) to the 17,21-Orthoester

1. To a solution of 1,4-pregnadiene-11β,17α,21-triol-3,20-dione 17,21-ethylorthopropionate (100 mg.) in methylene chloride (2.5 ml) at 0°C and under an atmosphere of nitrogen add with stirring trimethylsilyl iodide (45 mg., 0.0306 ml., 1 equivalent). Stir the reaction mixture for 30 minutes, then wash the solution with 0.1 N aqueous sodium thiosulfate, then with water. Dry the methylene chloride solution over magnesium sulfate and evaporate. Chromatograph the resultant residue on silica gel by the thin layer technique developing with chloroform/ethyl acetate (2:1). Identify the bands with ultraviolet light by comparison with known standards. Scrape off the band containing 21-iodo-21-desoxy-1,4-pregnadiene-11β,17α-diol-3,20-dione 17-propionate and elute with ethyl acetate. Evaporate the eluates to a residue of 21-iodo-21-desoxy-1,4-pregnadiene-11β,17α-diol-3,20-dione 17-propionate, yield 55 mg. (46% theory); m.p. 166°–169°C; $[\alpha]_D^{26}$ + 98.0° (chloroform).

2. Also scrape off a more polar band containing 1,4-pregnadiene-11β,17α-diol-3,20-dione 17-propionate, elute with ethyl acetate and evaporate the eluates to a residue of 1,4-pregnadiene-11β,17α-diol-3,20-dione 17-propionate, yield 13 mg. (14.5% theory).

F. Addition of Triphenylsilyl Iodide (1 equivalent) to the 21-Iodo-17-Propionate Derivative To a solution of 21-iodo-21-desoxy-1,4-pregnadiene-11β,17α-diol-3,20-dione 17-propionate (55 mg.) in methylene chloride (2 ml.) add triphenylsilyl iodide (40.3 mg., 1 equivalent). Stir the reaction mixture for 10 minutes, then wash the solution with 0.1 N aqueous sodium thiosulfate, then with water. Dry the methylene chloride solution over magnesium sulfate and evaporate. Triturate the resultant residue with ether and separate the resultant precipitate by filtration to give 1,4-pregnadiene-11β,17α-diol-3,20-dione 17-propionate.

EXAMPLE 2

9α-FLUORO-16α-METHYL-1,4-PREGNADIENE-11β,17α-DIOL-3,20-DIONE 17-PROPIONATE

A. Addition of Triphenylsilyl Iodide (3 equivalents) to the 17,21-Orthoester

1. To a solution of 9α-fluoro-16α-methyl-1,4-pregnadiene-11β,17α,21-triol-3,20-dione 17,21-ethylorthopropionate (94 mg.) in methylene chloride (3 ml.) add triphenylsilyl iodide (232 mg., 3 equivalents). Stir for 10 minutes, then wash the solution with 0.1 N aqueous sodium thiosulfate, then with water, dry the methylene chloride solution over magnesium sulfate and evaporate. Chromatograph the resultant residue on silica gel via thin layer chromatographic technique developing the plates with methylene chloride/ethyl acetate (2:1). Scrape off the band containing 9α-fluoro-16α-methyl-1,4-pregnadiene-11β,17α-diol-3,20-dione 17-propionate as identified under ultraviolet light by comparison with a known standard. Elute with ethyl acetate and evaporate the combined eluates to give a residue of 9α-fluoro-16α-methyl-1,4-pregnadiene-11β,17α-diol-3,20-dione 17-propionate; yield 25 mg. (29% theory); m.p. 214°–217°C; $[\alpha]_D^{26}$ + 37.4 (chloroform).

2. Treat 9α-fluoro-16α-methyl-1,4-pregnadiene-11β,17α,21-triol-3,20-dione 17,21-n-butylorthopropionate with triphenylsilyl iodide in the manner described in above Example 2A(1) to obtain 9α-fluoro-16α-methyl-1,4-pregnadiene-11β,17α-diol-3,20-dione 17-propionate.

B. Addition of Trimethylsilyl Iodide (5 equivalents) to the 17,21-Orthoester

To a solution of 9α-fluoro-16α-methyl-1,4-pregnadiene-11β,17α,21-triol-3,20-dione 17,21-ethylorthopropionate (100 mg.) in methylene chloride (5 ml.) at room temperature under an atmosphere of argon add trimethylsilyl iodide (0.143 ml., 5 equivalents). Stir for one minute, then wash the solution with 0.1 N aqueous sodium thiosulfate, then twice with water, dry over magnesium sulfate and evaporate in vacuo. Purify the resultant residue by chromatography on silica gel by thin layer technique developing with chloroform/ethyl acetate (2:1). Scrape off the band containing 9α-fluoro-16α-methyl-1,4-pregnadiene-11β,17α-diol-3,20-dione 17-propionate as identified under ultraviolet light by comparison with a known standard. Elute the band with ethyl acetate and evaporate the eluates to a residue comprising 9α-fluoro-16α-methyl-1,4-pregnadiene-11β,17α-diol-3,20-dione 17-propionate, yield 60 mg. (66% theory). Purify further by crystallization from acetone/hexane, yield of purified product 42 mg. (46% theory); m.p. 218°–223°C; $[\alpha]_D^{26} + 40°$ (chloroform).

EXAMPLE 3

11-OXYGENATED-9α-FLUORO-16β-METHYL-1,4-PREGNADIENE-17α-OL-3,20-DIONE 17-LOWER ALKANOATE

A.

9α-Fluoro-16β-Methyl-1,4-Pregnadiene-11β,17α-Diol-3,20-Dione 17-Propionate

Addition of Trimethylsilyl Iodide (5 equivalents) to the 17,21-Orthoester

To a solution of 9α-fluoro-16β-methyl-1,4-pregnadiene-11β,17α,21-triol-3,20-dione 17,21-n-ethylbutylorthopropionate (50 mg.) in methylene chloride (5 ml.) add trimethylsilyl iodide (100 mg., 0.068 ml.). Stir for 2 hours at room temperature, then wash the solution with 0.1 N aqueous sodium thiosulfate. Wash twice with water, dry over magnesium sulfate and evaporate. Chromatograph the resultant residue via thin layer chromatography developing with chloroform/ethyl acetate (2:1). Scrape off the band containing 9α-fluoro-16β-methyl-1,4-pregnadiene-11β,17α-diol3,20-dione 17-propionate as identified under ultraviolet light by comparison with a known standard. Elute with ethyl acetate and evaporate the eluate to a residue of 9α-fluoro-16β-methyl-1,4-pregnadiene-11β,17α-diol-3,20-dione 17-propionate.

B. Treat each of 9α-fluoro-16β-methyl-1,4-pregnadiene-17α,21-diol-3,11,20-trione 17,21-ethylorthovalerate and 6α,9α-difluoro16β-methyl-1,4-pregnadiene-11β,17α,21-triol-3,20-dione 17,21-ethylorthoacetate with trimethylsilyl iodide in the manner described in Example 3A. Isolate and purify each of the resultant products in a manner similar to that described to obtain 9α-fluoro16β-methyl-1,4-pregnadiene-17α-ol-3,11,20-trione 17-valerate and 6α,9α-difluoro-16β-methyl-1,4-pregnadiene-11β,17α-diol-3,20-dione 17-acetate, respectively.

EXAMPLE 4

9α,11β-DICHLORO-16α-METHYL-1,4-PREGNADIENE17α-OL-3,20-DIONE 17-PROPIONATE

A. Addition of Triphenylsilyl Iodide to the 17,21-Orthoester

1. Utilizing 3 Equivalents of Triphenylsilyl Iodide

To a solution of 9α,11β-dichloro-16α-methyl-1,4-pregnadiene-17α,21-diol-3,20-dione 17,21-ethylorthopropionate (108 mg.) in methylene chloride (1 ml.) add triphenylsilyl iodide (227 mg., 3 equivalents). Stir at room temperature for 15 minutes, then wash the solution with 0.1 N aqueous sodium thiosulfate, then twice with water, dry over magnesium sulfate and evaporate. Purify on silica gel via thin layer chromatographic technique developing with chloroform/ethyl acetate (3:1). Scrape off the band containing 9α,11β-dichloro-16α-methyl-1,4-pregnadiene17α-ol-3,20-dione 17-propionate as identified under ultraviolet light by comparison with a known standard, elute with ethyl acetate and evaporate the ethyl acetate eluates to a residue of 9α,11β-dichloro-16α-methyl-1,4-pregnadiene-17α-ol-3,20-dione 17-propionate; yield 48 mg. (48% theory); m.p. 221°-225°C; $[\alpha]_D^{26} + 110.8°$ (chloroform).

2. Utilizing 1 Equivalent of Triphenylsilyl Iodide

To a solution of 9α,11β-dichloro-16α-methyl-1,4-pregnadiene-17α-ol-3,20-dione 17,21-ethylorthopropionate (102 mg.) in methylene chloride (4 ml.) add triphenylsilyl iodide (76 mg., 1 equivalent). Stir at room temperature for 10 minutes, then wash the solution with 0.1 N aqueous sodium thiosulfate, then twice with water. Dry over magnesium sulfate and evaporate. Purify the resultant residue on silica gel via thin layer chromatographic techniques developing the plates with chloroform/ethyl acetate (9:1). Scrape off the layer containing 9α,11β-dichloro-16αmethyl-1,4-pregnadiene-17α-ol-3,20-dione 17-propionate as identified under ultraviolet light by comparison with a known standard. Elute with ethyl acetate and evaporate the eluates to a residue of 9α,11β-dichloro-16α-methyl-1,4-pregnadiene-17α-ol3,20-dione 17-propionate; yield 23 mg. (25% theory); m.p. 224°-227°C.

B. Addition of Trimethylsilyl Iodide (5 equivalents) to the 17,21-Orthoester

1. To a solution of 9α,11β-dichloro-16α-methyl-1,4-pregnadiene17α,21-diol-3,20-dione 17,21-ethylorthopropionate (280 mg.) in methylene chloride (5 ml.) at room temperature add trimethylsilyl iodide (0.34 ml., 5 equivalents). Stir for 1 minute, then wash the solution with 0.1 N aqueous sodium thiosulfate, then twice with water. Dry over magnesium sulfate and evaporate. Purify the resultant residue on silica gel via thin layer techniques developing the plates with chloroform/ethyl acetate (9:1). Scrape off the band containing 9α,11β-dichloro-16α-methyl-1,4-pregnadiene-11β-ol-3,20-dione 17-propionate as identified under ultraviolet light by comparison with a known standard. Elute with ethyl acetate and evaporate the mixture to a residue of 9α,11β-dichloro-16α-methyl-1,4-pregnadiene-17α-ol-3,20-dione 17-propionate; yield 141 mg. (55% theory); m.p. 216°-219°C; $[\alpha]_D^{26} + 118°$ (dioxane).

2. In the procedures of Examples 4A and 4B utilize as starting compound 9α,11β-dichloro-16α-methyl-1,4- pregnadiene-17α,21-diol3,20-dione 17,21-n-butylorthopropionate to obtain 9α,11β-dichloro 16α-methyl-1,4-pregnadiene-17α-ol-3,20-dione 17-propionate.

C. Addition of Trimethylsilyl Iodide (1 equivalent) to the 17,21-Orthoester

1. To a solution of 9α,11β-dichloro-16α-methyl-1,4-pregnadiene 17α,21-diol-3,20-dione 17,21-ethylorthopropionate (280 mg.) in methylene chloride (5 ml.) at room temperature add trimethylsilyl iodide (0.068 ml., 1 equivalent). After 1 minute wash the solution with 0.1 N aqueous sodium thiosulfate then twice with water. Dry over magnesium sulfate and evaporate. Purify the resultant residue by chromatography on silica gel by thin layer technique developing with chloroform/ethyl acetate (9:1). Scrape off the band containing 9α,11β-dichloro-21-iodo-21-desoxy-16α-methyl 1,4-pregnadiene-17α-ol-3,20-dione 17-propionate as identified under ultraviolet light. Elute with ethyl acetate and evaporate the eluate to a residue of 9α,11β-dichloro-21-iodo-21-desoxy 1,4-pregnadiene-3,20-dione 17-propionate; yield 89 mg. (27.5% theory); m.p. 150°C (decomp.); $[\alpha]_D^{26}$ 118.7° dioxane); nmr (DMSO-$d_6$); δ 1.05 ($C_{13}$-$CH_3$, s); 1.68 ($C_{10}$-$CH_3$, s); 4.05 ($C_{21}$-$CH_2$, s)

2. Scrape off the more polar band containing 9α,11β-dichloro 16α-methyl-1,4-pregnadiene-17α-ol-3,20-dione 17-propionate, elute with ethyl acetate and evaporate to a residue of 9α,11β-dichloro16α-methyl-1,4-pregnadiene-17α-ol-3,20-dione 17-propionate, yield 62 mg. (24% theory).

D. Addition of the Trimethylsilyl Iodide Reagent (1 equivalent) to the 21-Iodo 17α-Propionate Derivative 1. Addition of Trimethylsilyl Iodide To a solution of 9α,11β-dichloro/21/iodo-16α-methyl-1,4-pregnadiene-17α-ol-3,20-dione 17-propionate (29 mg.) in methylene chloride (1 ml.) add trimethylsilyl iodide (10 mg., ≡ 0.007 ml., 1 equivalent). Stir for 10 minutes at room temperature, then wash the reaction mixture with 0.1 N aqueous sodium thiosulfate, then twice with water. Dry over sodium sulfate and evaporate to a residue of 9α,11β-dichloro-16α-methyl-1,4-pregnadiene-17α-ol-3,20-dione 17-propionate; yield 18 mg. (100% theory); 215°-218°C.

2. Addition of Triphenylsilyl Iodide (1 equivalent)

To 9α,11β-dichloro-21-iodo-16α-methyl-1,4-pregnadiene 17α-ol-3,20-dione 17-propionate (29 mg.) in methylene chloride (1 ml.) add triphenylsilyl iodide (19 mg., 1 equivalent). Stir the reaction mixture for 10 minutes at room temperature, then isolate and purify the resultant product in a manner similar to that described in above Example 4D(1). Triturate the residue obtained on evaporation of the chloroform solution with ether and filter the resultant precipitate of 9α,11β-dichloro-16α-methyl-1,4-pregnadiene-17α-ol-3,20-dione 17-propionate; yield 14 mg. (78% theory); m.p. 214°-220°C.

EXAMPLE 5

CONVERSION OF OTHER 1,4-PREGNADIENE-3,20-DIONE 17,21-ORTHOESTERS TO THE CORRESPONDING 21-DESOXY-1,4-PREGNADIENE-17α-OL-3,20-DIONE 17-ACYLATE

1. In a manner similar to that described in Examples 1A and 1B treat each of the following 1,4-pregnadiene-3,20-dione 17,21-orthoesters with either 3 equivalents of triphenylsilyl iodide or 5 equivalents of trimethylsilyl iodide.
   1. 16α-methyl-1,4-pregnadiene-11β,17α,21-triol-3,20-dione 17,21-n-butylorthopropionate,
   2. 9α-fluoro-16α-methyl-1,4-pregnadiene-11β,17α,21-triol-3,20-dione 17,21-methylorthobenzoate,
   3. 9α,11β-dichloro-16α-methyl-1,4-pregnadiene17α,21-diol-3,20-dione 17,21-methylorthobenzoate, and
   4. 9α,11β-dichloro-16α-methyl-1,4-pregnadiene17α,21-diol-3,20-dione 17,21-n-butylorthovalerate.

2. Isolate and purify each of the resultant products in a manner similar to that described in Examples 1A and 1B to obtain, respectively,
   1. 16α-methyl-1,4-pregnadiene-11β,17α-diol-3,20dione 17-propionate,
   2. 9α-fluoro-16α-methyl-1,4-pregnadiene-11β,17α-diol-3,20-dione 17-benzoate,
   3. 9α,11β-dichloro-16α-methyl-1,4-pregnadiene17α-ol-3,20-dione 17-benzoate, and
   4. 9α,11β-dichloro-16α-methyl-1,4-pregnadiene17α-ol-3,20-dione 17-valerate.

EXAMPLE 6

PREPARATION OF 21-DESOXY-4-PREGNENE-17α-OL-3,20-DIONE 17-ACYLATE

In Examples 1-5, by substituting for the 1,4-pregnadiene-17α,21-diol-3,20-dione 17,21-orthoester starting compound the corresponding 1,2-dihydro analog thereof, there is obtained the corresponding 1,2-dihydro analog of the resulting 21-desoxy1,4-pregnadiene-17α-ol-3,20-dione 17-acylate product, i.e. in the procedure analogous to Examples 1A-1D and 1F there is obtained 4-pregnene-11β,17α-diol-3,20-dione 17-propionate; in the procedure analogous to Example 1E there is obtained a mixture of 4-pregnene-11β,17α-diol-3,20-dione 17-propionate, the 11-trimethylsilyl ether thereof, and the 21-iodo-4-pregnene-11β,17α-diol-3,20dione 17-propionate; in the procedure analogous to Example 2 there is obtained 9α-fluoro-16α-methyl-4-pregnene-11β,17α-diol3,20-dione 17-propionate; in the procedure analogous to Example 3 there is obtained 9α-fluoro-16β-methyl-4-pregnene-11β,17α-diol3,20-dione 17-propionate, 9α-fluoro-16β-methyl-4-pregnene-17α-ol3,11,20-trione 17-valerate and 6α,9α-difluoro-16β-methyl-4-pregnene11β,17α,21-triol-3,20-dione 17-acetate; in the procedure analogous to Examples 4A, 4B and 4D there is obtained, respectively, 9α,11β-dichloro-16α-methyl-4-pregnene-17α-ol-3,20-dione 17-propionate; in the procedure analogous to Example 4C there is obtained a product mixture of 9α,11β-dichloro-4-pregnene-17α-ol3,20-dione 17-propionate and 9α,11β-dichloro-21-iodo-4-pregnene17α-ol-3,20-dione 17-propionate; in the procedure analogous to Example 5 there is obtained, respectively, 16α-methyl-4-pregnene11β,17α-diol-3,20-dione 17-propionate, 9α-fluoro-16α-methyl-4-pregnene-11β,17α-diol-3,20-dione 17-butyrate, 9α,11β-dichloro16α-methyl-4-pregnene-17α-ol-3,20-dione 17-benzoate and 9α,11βdichloro-16α-methyl-4-pregnene-11β,17α-diol-3,20-dione 17-valerate.

EXAMPLE 7

PREPARATION OF 21-DESOXY-1,4,6-PREGNATRIENE-17α-OL-3,20-DIONE 17-ACYLATES

A. 1,4,6-Pregnatriene-11β,17α-Diol-3,20-Dione 17-Propionate

Treat 1,4,6-pregnatriene-11β,17α,21-triol-3,20-dione 17,21-n-butylorthopropionate in methylene chloride with either triphenylsilyl iodide (3 equivalents) according to the procedure of Example 1A or with trimethylsilyl iodide (5 equivalents) according to the procedure of Example 1B. Isolate and purify the resultant product in a manner similar to that described to obtain 1,4,6-pregnatriene-11β,17α-diol-3,20-dione 17-propionate.

B. In similar manner treat the corresponding 6-dehydro analogs of each of the starting compounds in Examples 1–5 with either triphenylsilyl iodide or trimethylsilyl iodide to obtain the corresponding 6-dehydro analog of the resulting product.

I claim:

1. The process for the preparation of a 21-desoxy-17-acyloxy-20-ketopregnene which comprises the reaction of a pregnane derivative selected from the group consisting of 17,21-dihydroxy-20-ketopregnene 17,21-orthoester and a 21-iodo-21-desoxy-17acyloxy-20-ketopregnene with an iodide reagent selected from the group consisting of triphenylsilyl iodide, tri-lower alkylsilyl iodide and triphenylmethyl iodide, in an organic solvent.

2. The process of claim 1 wherein said iodide reagent is triphenylsilyl iodide or trimethylsilyl iodide.

3. The process of claim 1 which comprises the reaction of a 17,21-dihydroxy-20-ketopregnene 17,21-orthoester with at least 2 moles of said iodide reagent.

4. The process of claim 3 wherein said iodide reagent is triphenylsilyl iodide or trimethylsilyl iodide.

5. The process of claim 1 which comprises the reaction of a 17,21-dihydroxy-20-ketopregnene 17,21-orthoester selected from the group consisting of a compound defined by formula I:

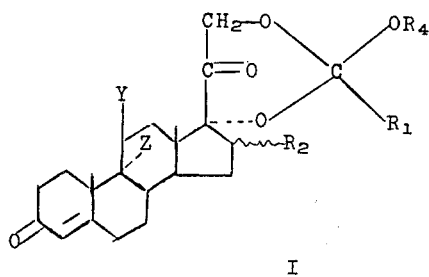

I wherein Y is hydrogen, oxo, hydroxy, lower alkanoyloxy, chlorine or fluorine;

Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;

R₁ is alkyl of 1 to 8 carbon atoms, or phenyl;

R₂ is hydrogen, α-methyl, β-methyl, α-acyloxy of the formula

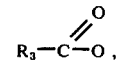

wherein R₃ is a lower alkyl having 1 to 8 carbon atoms;

R₄ is alkyl having 1 to 4 carbon atoms;

and the 1-dehydro-, 6-dehydro- and 1,6-bis-dehydro analogs of the compounds of formula I; with at least two molar equivalents of iodide reagent selected from the group consisting of triphenylsilyl iodide and trimethylsilyl iodide.

6. The process of claim 5 wherein the 17α,21-dihydroxy20-ketopregnene 17,21-orthoester is a compound of the formula:

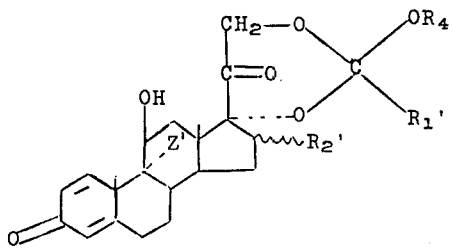

wherein

Z' is hydrogen or fluorine;

R₁' is an alkyl of from 1 to 4 carbon atoms;

and R₂' is hydrogen or methyl.

7. The process of claim 6 for the preparation of 1,4pregnadiene-11β,17α-diol-3,20-dione 17-propionate which comprises the reaction of a 1,4-pregnadiene-11β,17α,21-triol-3,20-dione 17,21-alkylorthopropionate with triphenylsilyl iodide or trimethylsilyl iodide, in methylene chloride.

8. The process of claim 1 wherein said pregnene derivative is a 17,21-dihydroxy-20-ketopregnene 17,21-orthoester and wherein said iodide reagent is tri-lower alkylsilyl iodide, which comprises the reaction of said 17,21-dihydroxy-20-ketopregnene 17,21-orthoester with less than two molar equivalents of a tri-lower alkylsilyl iodide whereby is obtained a product mixture comprising a 21-desoxy-17-acyloxy-20-ketopregnene and a 21-iodo-21-desoxy17-acyloxy-20-ketopregenene.

9. The process of claim 8 wherein said tri-lower alkylsilyl iodide is trimethylsilyl iodide.

10. The process of claim 8 including the step of isolating the 21-iodo-21-desoxy-17-acyloxy-20-ketopregnene thereby formed.

* * * * *

UNITED STATES PATENT OFFICE
CERTIFICATE OF CORRECTION

Patent No. 3,980,680                  Dated September 14, 1976

Inventor(s) Michael J. Green

It is certified that error appears in the above-identified patent and that said Letters Patent are hereby corrected as shown below:

Column 9, line 14, "-orthoenzoate" should read ---orthobenzoate---.
Column 12, line 1, "(45 mg., 0.0306 ml.," should read ---45 mg., = 0.0306 ml.,---.
Column 13, line 43, "100 mg., 0.086 ml.) should read ---(100 mg., = 0.068 ml.)---.
Column 15, line 23, "dioxane)," should read ---(dioxane),---; line 37, "9α,11β dichloro/21/iodo" should read ---9α,11β-dichloro-21-iodo---.

Signed and Sealed this

Eighteenth Day of January 1977

[SEAL]

Attest:

RUTH C. MASON
Attesting Officer

C. MARSHALL DANN
Commissioner of Patents and Trademarks